United States Patent [19]
Tsals

[11] Patent Number: 6,000,548
[45] Date of Patent: Dec. 14, 1999

[54] DRUG DELIVERY KIT AND METHOD OF PACKAGING THE SAME

[75] Inventor: Izrail Tsals, Sudbury, Mass.

[73] Assignee: Elan Corporation, plc, Dublin, Ireland

[21] Appl. No.: 09/102,841

[22] Filed: Jun. 23, 1998

Related U.S. Application Data

[63] Continuation of application No. 08/881,548, Jun. 24, 1997.

[30] Foreign Application Priority Data

Jun. 16, 1997 [IE] Ireland ..................... 970444

[51] Int. Cl.⁶ .................................. B65D 69/00
[52] U.S. Cl. ..................... 206/570; 206/438; 206/564; 206/461; 206/807
[58] Field of Search ..................... 206/570, 564, 206/438, 461, 471, 807, 571, 539; 220/525

[56] References Cited

U.S. PATENT DOCUMENTS

| | | | |
|---|---|---|---|
| 3,013,656 | 12/1961 | Murphy, Jr. ........................ | 206/570 |
| 3,746,155 | 7/1973 | Seeley ................................ | 206/571 |
| 4,085,845 | 4/1978 | Perfect ............................... | 206/564 |
| 4,522,302 | 6/1985 | Paikoff . | |
| 4,915,233 | 4/1990 | Smith .................................. | 206/571 |
| 5,098,391 | 3/1992 | Pantages et al. ................... | 604/159 |
| 5,178,282 | 1/1993 | Williams . | |
| 5,318,543 | 6/1994 | Ross et al. ......................... | 604/175 |
| 5,441,152 | 8/1995 | Estes ................................... | 206/570 |
| 5,609,248 | 3/1997 | Rohrbough et al. . | |

FOREIGN PATENT DOCUMENTS 2721498 12/1995 France .
WO 9218177 10/1992 WIPO .

*Primary Examiner*—Paul T. Sewell
*Assistant Examiner*—Nhan T. Lam
*Attorney, Agent, or Firm*—Kathleen L. Maher

[57] ABSTRACT

An improved drug delivery kit and method of packaging the same. The method includes providing a tray having first and second recesses for receiving a drug delivery device and drug cartridge respectively, and an opening in the tray within the second recess, placing the drug delivery device in the first recess, covering the tray with a sealable material, sealing the material to the tray so as to create a seal around the first and second recesses, so as to isolate the first recess from the second recess, sterilising the tray, and inserting the drug cartridge through the opening and into second recess. The opening is sized such that insertion of the drug cartridge through the opening and into the second recess elastically stresses the tray and removal of the drug cartridge from the opening irreversibly deforms the tray, thereby creating a tamper-proof drug delivery kit.

3 Claims, 4 Drawing Sheets

DRUG DELIVERY KIT AND METHOD OF PACKAGING THE SAME

This application is a continuation of Ser. No. 08/881,548 filed Jun. 24, 1997.

TECHNICAL FIELD

This invention relates to an improved drug delivery kit and an improved method of packaging a drug delivery kit. In particular, the invention relates to the assembly and method of packaging a sterilised empty drug delivery device and filled drug cartridge. The invention also relates to an improved drug cartridge.

BACKGROUND OF THE INVENTION

At present, the health industry is focused on providing more effective ways for patients to have more control over their own medication. One such way of providing more control to patients is to allow patients to self-medicate parenteraly drugs that cannot be delivered in other less invasive ways (such as orally). Self medication may be in the form of a syringe (as with diabetics who regularly self-inject insulin) or other drug delivery devices having an infusion mechanism and needle for penetrating the skin.

One such drug delivery device is disclosed in U.S. Pat. No. 5,527,288, which is incorporated herein by reference, for an intradermal drug delivery device and method for intradermal delivery of drugs. Such a device includes a housing, a drug reservoir, an electrolytic cell and a needle. When activated, the electrolytic cell generates a gas which presses against the reservoir and causes the drug to move out of the reservoir, through the needle and into the patient.

In some cases, these devices are intended to be packaged with the reservoir being empty and sterilised separately from the drug. Sterilisation of the drug itself with the drug delivery device is usually not desired because the sterilisation techniques used today for drug delivery devices may affect the drug's potency or otherwise adversely affect the drug itself. Thus, it is desirable to sterilise the drug delivery device and drug cartridge separately.

Sterilisation of empty drug delivery devices often occur in the packaging. Where the drug delivery device is provided with a filled drug cartridge, it is preferred that the drug delivery device be sterilised in its packaging, then the filled, sterilised drug cartridge is added to the drug delivery kit (the kit containing a drug delivery device, a filled drug cartridge and related packaging). The term "drug cartridge" herein refers to a drug container having a stopper, or plunger (typically made of natural or synthetic rubber) to seal the contents thereof.

When the drug delivery device and related packaging are sterilised separately from the drug cartridge, a problem arises in placing the drug cartridge in the kit without compromising the sterility of the device or cartridge, while enabling the device and cartridge to be packaged as a kit. Moreover, if the cartridge is packaged with the kit, there must be a way to incorporate the cartridge within the kit to prevent tampering.

With respect to drug stored in a cartridge, there is an additional packaging problem with maintaining sterility of the outer surface of the plunger when the drug is to be withdrawn from the cartridge for use. In the past, a drug delivery device was filled with drug by means of an Ogle style injection system. Such a system uses a shell cartridge having a plunger and a protective cap. The protective cap was typically applied to the top of the cartridge. This cap maintained the sterility of the outer surface of the plunger before use. However, the use of a protective cap is impractical in that it requires the application of the protective cap in the sterile environment. Such a process is time consuming and requires specialized production equipment, and as a result is expensive. Thus, there is a need for a way of maintaining the sterility of the outer surface of a drug cartridge plunger that is compatible with existing high speed cartridge-filling equipment.

In addition to the other problems associated with prior art drug delivery kits, the use of syringes to transfer drug to a drug delivery device is inherently dangerous. An exposed hypodermic needle may cause injury if the user or caregiver is accidentally pricked by the needle. Furthermore, contact with the needle by an unskilled worker could result in microbial contamination of the drug which may lead to infection.

There are at present improved drug transfer systems to reduce the risk of injury and infection caused by filling a drug delivery device with a standard syringe. Such filling systems and methods directly transfer the drug from a standard drug cartridge to the drug delivery device without exposing the patient or caregiver to any needles. One such improved filling system is disclosed in applicant's copending application filed May 6, 1997, which is incorporated herein by reference.

Such improved filling system transfers drug from a drug cartridge to a drug delivery device. A standard drug cartridge seals the drug within a drug container by means of a solid rubber plunger. The improved filling systems require a uniquely shaped rubber plunger to enable the needle used in the drug transfer to penetrate the cartridge without being exposed to the user/caregiver when the transfer mechanism is removed upon completion of the filling process.

In addition, as with prior art drug transfer systems, the sterility of the outer surface of the plunger must be maintained. This posed a difficult problem in using existing production line equipment to maintain the sterility of the outer surface of the plunger while utilising existing production line equipment to accomplish this task. As set forth in more detail above, prior art drug cartridges use a protective cap placed on the top of the drug cartridge. This method is costly and slow as it must be as an additional step after the insertion of the plunger into the drug container but must be done in a sterile environment to maintain sterility of the outer surface of the plunger until the cap is in place. Such a method required significant manual labour or use of low speed production equipment. In addition, the present filling lines leave a certain volume of air in the cartridge which is an unwanted commodity when the drug is being transferred. Until now, there has been no means for maintaining the sterility of the outer surface of a plunger on a drug cartridge by use of existing, high speed production equipment, while leaving no air between the plunger and sterility maintenance means.

Thus, there is a need to effectively assemble a drug delivery kit having a drug cartridge and a drug delivery device after the device has been sterilised.

There is a further need to provide an improved method of packaging a filled drug cartridge with a drug delivery device without subjecting the drug to the same sterilisation process as that of the device.

There is a further need to assemble a sterilised drug delivery device and a drug cartridge as a drug delivery kit while preventing tampering and/or contamination.

There is yet a further need to provide an improved method for maintaining sterility of the outer surface of the plunger of a drug cartridge prior to transfer of the drug to the drug delivery device.

There is still a further need to provide a method of assembling an improved drug cartridge that is tamper proof and that utilises existing production equipment in the assembly.

SUMMARY OF THE INVENTION

The present invention overcomes these and other disadvantages associated with prior art drug delivery kits, drug cartridges and methods of assembling the same. Stated generally, the present invention provides for an improved method of packaging a drug delivery kit. The method includes providing a tray having a first recess for receiving a drug delivery device and a second recess for receiving a drug cartridge, placing the drug delivery device in the first recess, covering the first and second recesses with a sealable material, creating a seal between the sealable material and the first recess, so as to isolate the first recess from the second recess, providing an opening in the tray within the second recess, sterilising the tray containing the drug delivery device, and inserting the drug cartridge through the opening and into the second recess.

When the drug cartridge of the present invention is inserted through the opening into the tray, the sealing material near the second recess allows the insertion of the cartridge. Typically, the cartridge and delivery device are accessed by the user or caregiver by removing the sealable material from the tray. However, if the cartridge is removed from the tray through the opening, the tray will permanently deform thus providing proof of tampering, and thus providing a safe, effective and efficient drug delivery kit and method of packaging the same.

Another aspect of the present invention is directed to an improved drug cartridge. The drug cartridge of the present invention includes a container containing drug therein, a plunger, and a means for maintaining the sterility of the outer surface of the plunger. The first plunger is adjacent to the drug. The sterility maintenance means is connected to the plunger. It is preferred that the sterility maintenance means is a cup having a first annular end for fitting into the annular grove located on the outer surface of the plunger. The second end of the cup is a protuberance. The protuberance receives the small end of a flared cap. The circumference of the small end of the cap is less than that of the opposing end. This is shaped so that when the drug cartridge is removed from the kit tray through the opening in the tray it causes the tray to permanently deform, thus providing evidence of tampering. A seal may be place over the opening after the cartridge is inserted to further discourage tampering and provide further proof of tampering if it occurs.

An alternative embodiment of the improved drug cartridge of the present invention includes a container containing drug therein, a first plunger, a second plunger and a means for removing the second plunger from the cartridge before use.

To transfer the drug from the cartridge, the cap and cup are removed and placed within the transfer assembly where a needle penetrates the plunger to transfer the drug from the cartridge to the drug delivery device. The plunger and cap assembly enables the user to transfer drug while maintaining sterility of the entire system.

Thus, it is an object of the present invention to provide a method of effectively and efficiently packaging a drug with a drug delivery device after the device has been sterilised.

It is a further object of the present invention to provide an improved method of packaging a drug with a drug delivery device without subjecting the drug to the same sterilisation process as that of the device.

It is a further object of the present invention to provide a method to package a drug and a sterilised drug delivery device together to prevent tampering and/or contamination.

It is yet a further object of the present invention to provide an improved drug cartridge that maintains sterility of the plunger prior to transfer of the drug to the drug delivery device using an improved filling method.

Other objects, features and advantages of the present invention will be apparent upon reading the following specification taken in conjunction with the drawings and appended claims.

BRIEF DESCRIPTION OF THE DRAWINGS

The invention will be further illustrated by the following description of embodiments thereof, given by way of example only with reference to the accompanying drawings, in which.

DETAILED DESCRIPTION OF THE INVENTION

Figure 1:
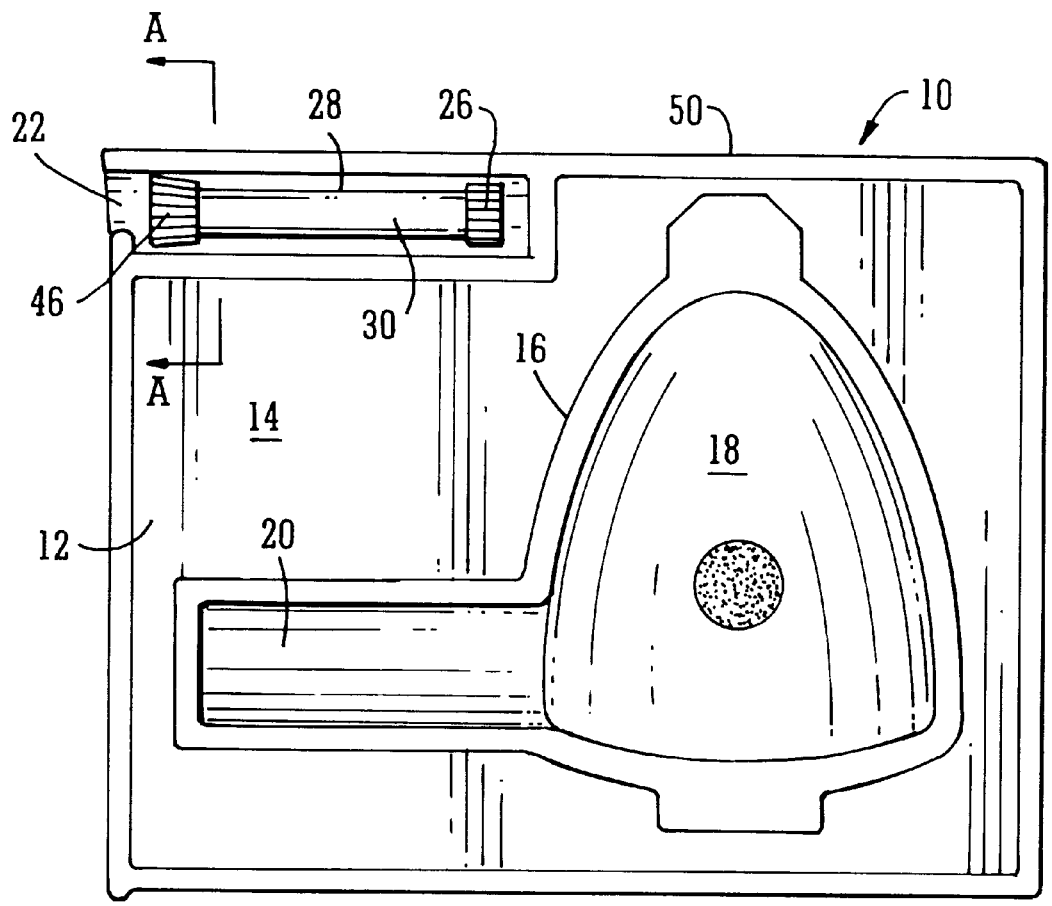
FIG. 1 is a top view of the drug delivery kit of the present invention.

Referring now in more detail to the drawings, in which like numerals refer to like parts throughout the several views, FIG. 1 indicates a drug delivery kit 10. The kit 10 contains a tray 12 having a top surface 14. The top surface 14 includes a first recess 16 for receiving a drug delivery device 18 and an attached drug transfer subsystem (not shown). The first recess 16 is shaped similarly to the drug delivery device 18 and transfer subsystem to support and hold the items within the tray 12.

Figure 2:
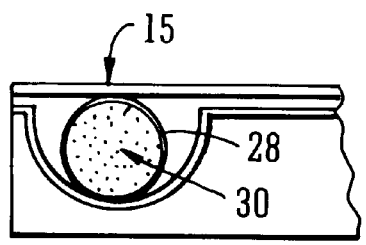
FIG. 2 is a partial sectional side view of preferred embodiment of FIG. 1 taken along line A—A.

The tray 12 further includes a second recess 22 also accessible from the top surface 14 of the tray. The second recess 22 receives a drug cartridge 26, as shown in FIG. 2. When assembled, the tray 12 is covered with a sheet of sealable material 15 (preferably Tyvek™ manufactured by the Dupont Corporation).

Figure 3:
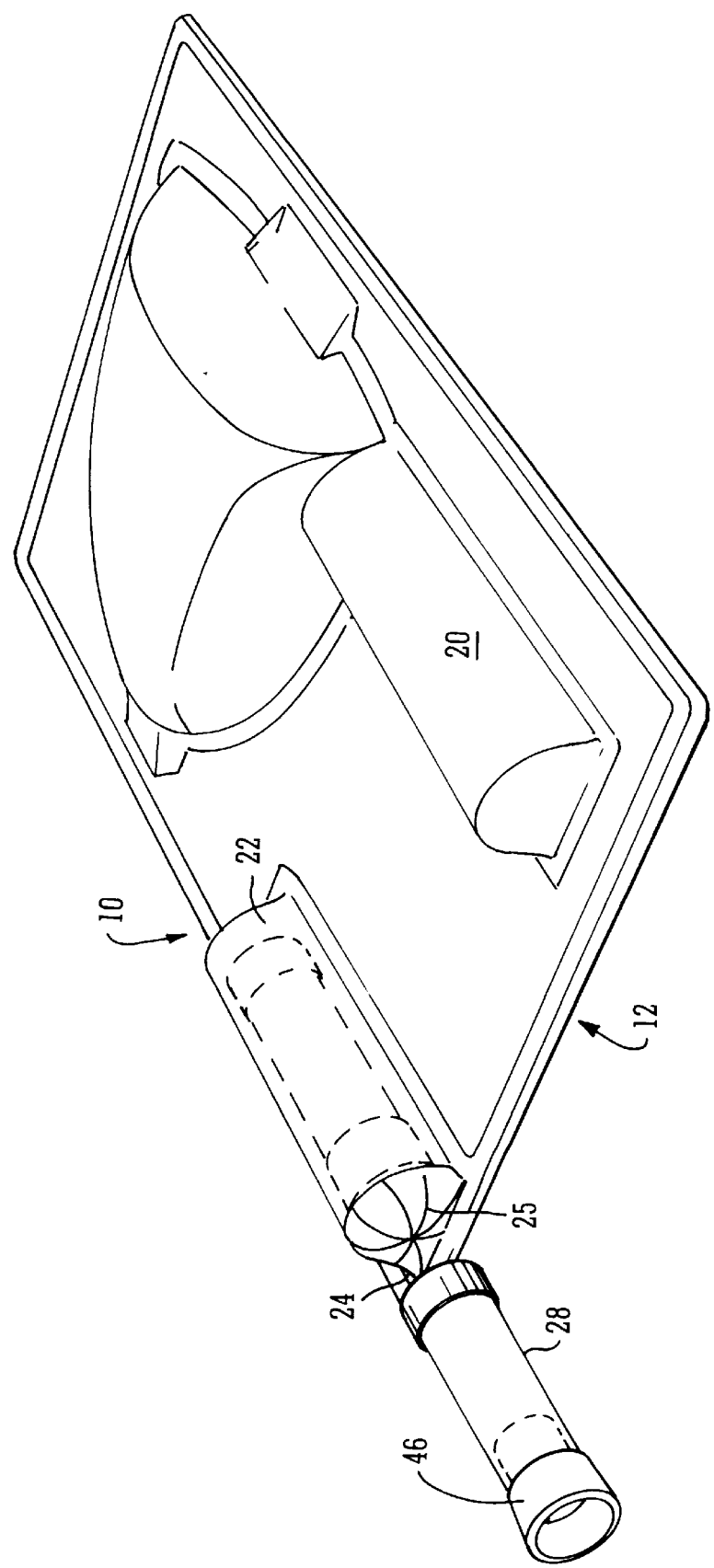
FIG. 3 is a partial perspective view of the assembly of the drug delivery kit of the present invention.

The tray 12 has an opening 24 on the side thereof. The opening 24 is in the form of a series of radially extending slits 25, as shown in FIG. 3. The opening 24 is sized to receive the drug cartridge 26.

Figure 4:
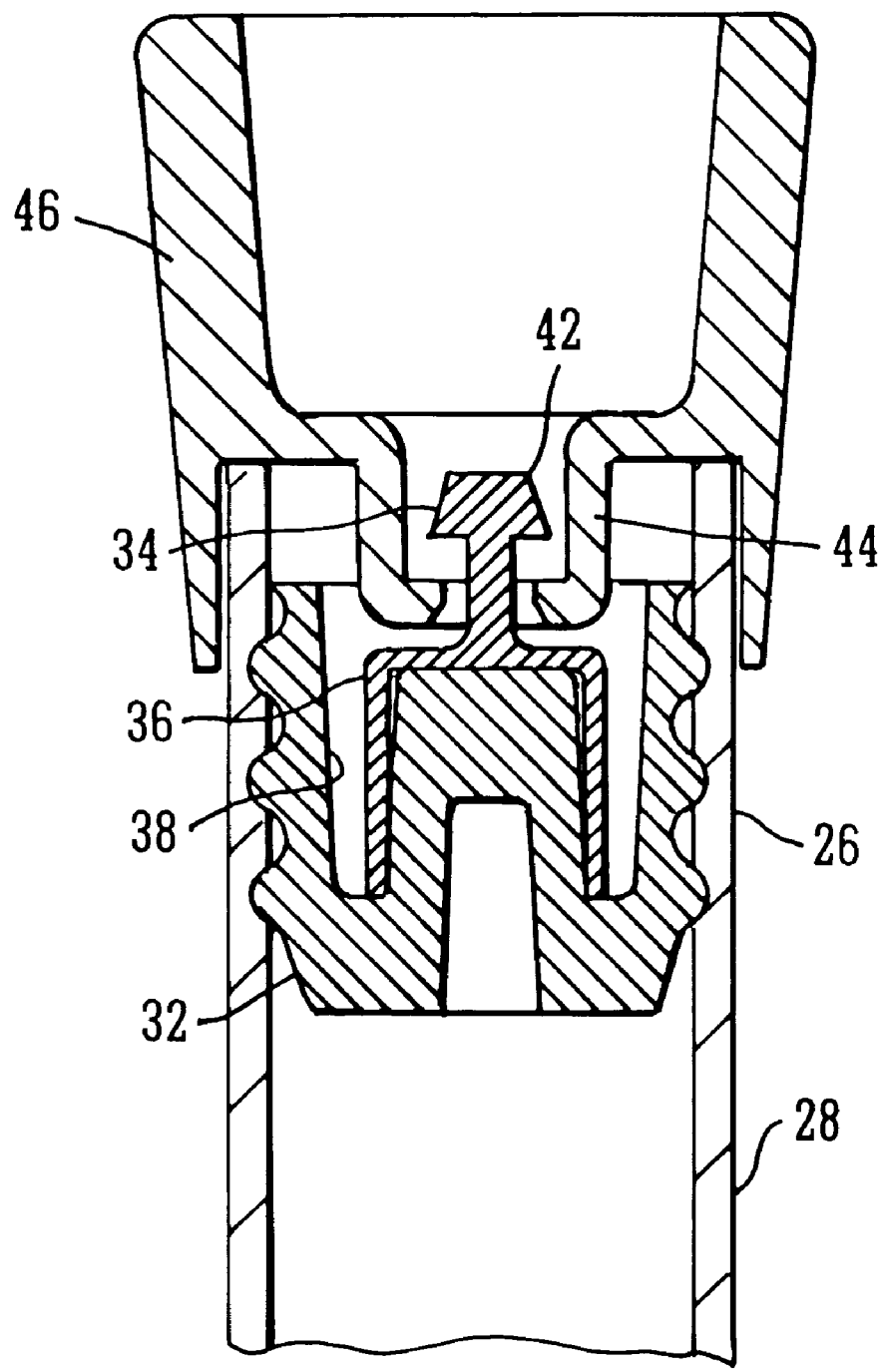
FIG. 4 is a detailed sectional view of a portion of the drug cartridge of the present invention.

The drug cartridge 26 of the present invention includes a container 28 having drug 30 contained therein. The drug cartridge 26 further includes a plunger 32 and a cup 34, as shown in FIG. 4. The plunger 32 is adjacent to the drug 30 within the cartridge 28, and the cup is adjacent to the outer surface of the plunger. This arrangement enables the sterility of the outer surface of the plunger 32 to be maintained. The cup and plunger may be sterilised as an assembly prior to being assembled with the container 28 and drug 30 so that the outer surface of the plunger will be maintained.

The cup 34 has an annular end 36 for fitting into an annular groove 38 in the plunger 32. The cup 34 also has a second end 40 having a single protuberance 42. The protuberance 42 is shaped to be received into the first end 44 of an end cap 46. The side surface 48 of the end cap 46 is preferably flared, as shown in FIG. 3. The shape of the end cap 46 once it is packaged within the kit 10 enables the kit to become tamper-proof, as will be explained in detail below.

The maintenance of the sterility of the outer surface of the plunger is important in the transfer of the drug 30 to the device 18. More importantly, the arrangement of the present drug cartridge allows for the assembly of a drug cartridge using existing high speed production equipment while maintaining the sterility of the outer surface of the plunger.

To package the kit 10, the tray 12 is oriented with the top surface 14 facing up, as shown in FIG. 1. The drug delivery device 18 with an attached drug transfer system (not shown) is placed within the first recess 16. The sheet 15 of sealable material is placed on the top surface 14 of the tray 12. Heat is applied to seal the sheet 15 around the edges of the top surface 14 of the tray 12 and between the first recess 16 and the second recess 22. The seal 50 must isolate the first recess 16 from the second recess 22. The tray 12 having the drug delivery device 18 therein is then sterilised.

Figure 5:
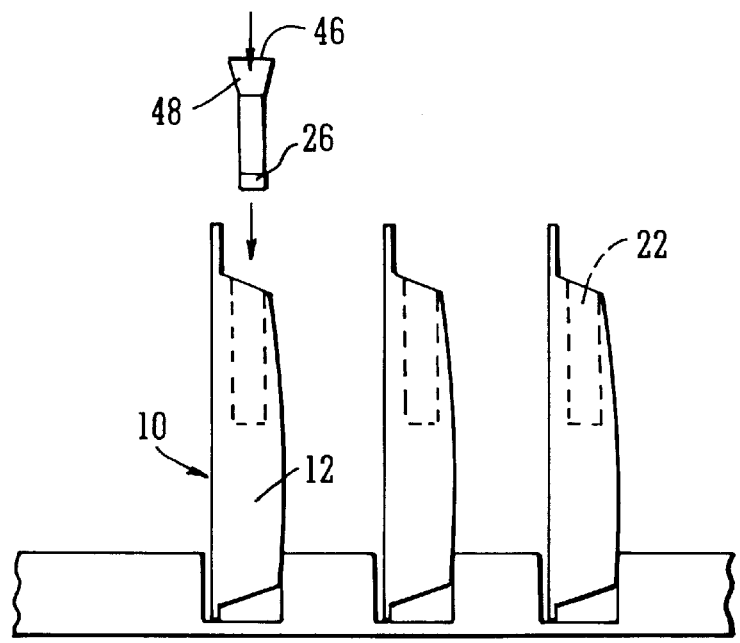
FIG. 5 is a side view of the preferred embodiment of FIG. 1 as it is being assembled.

For mass production of the kit 10, the sealed tray 12 is then placed on its side on a conveyor belt (not shown) with the second recess 22 and opening 24 facing upward as shown in FIG. 5. The drug cartridge 26 is inserted through the opening 24 and into the second recess 22 with the end cap 46 facing upward. The opening 24 is shaped to allow easy passage of the cartridge 26 therethrough. However, as the end cap 46 passes through the opening 24, the flared angle of the side surface 48 elastically stresses the opening but nonetheless allows complete passage therethrough.

Once the drug cartridge 26 and end cap 46 pass completely through the opening 24, it is difficult to remove the drug cartridge 26 through the opening without permanently deforming the opening and radially extending slots 15. Thus, any premature removal of the drug cartridge 26 through the opening 24 or by removal of even a portion of the sealed sheet 15 would provide obvious evidence of tampering which would result in disposal of the entire kit 10. Kits 10 fully intact provide assurance to the user that there has been no tampering and that the kit is safe from contamination.

The drug cartridge 26 is used in connection with improved filling systems. The drug cartridge 26 of the present invention maintains sterility of the drug during transfer of the drug 30 employing such a system. Such a system is disclosed in an copending application filed May 6, 1997 and is fully incorporated herein by reference.

Figure 6:
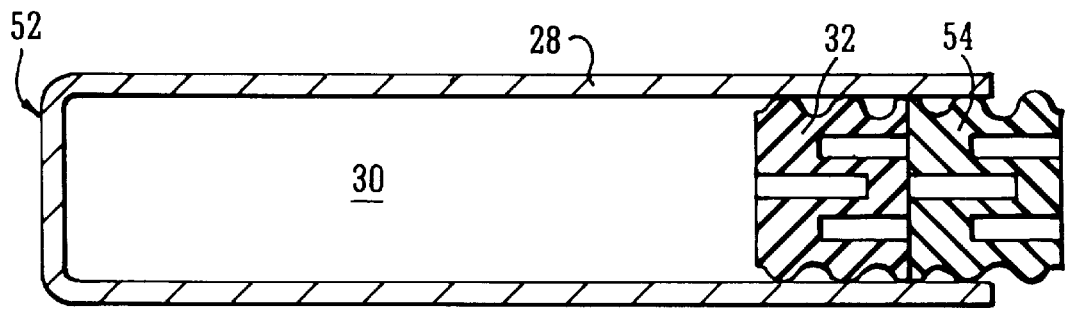
FIG. 6 is a sectional view of a first alternative embodiment of the drug cartridge of the present invention.

A first alternative embodiment 52 of the drug cartridge is shown in FIG. 6. In lieu of a cup 24 and end cap 46 assembly, the outer surface of the plunger 32 would be adjacent to a second plunger 54. This second plunger 54 could be removed manually or with a number of devices for quickly and easily removing the plunger prior to transfer of the drug.

It should be understood that the foregoing relates only to preferred embodiments of the present invention and that numerous modifications or alterations may be made therein without departing from the spirit and scope of the invention as set forth in the appended claims.

I claim:
1. An improved drug delivery kit comprising:
   a tray having first and second recesses;
   a sterilised drug delivery device located in the first recess;
   a drug cartridge located in the second recess, the drug cartridge having a length and a width, the length being greater than the width;
   a sheet of sealable material covering the tray so as to seal around the first and second recesses and isolate the first recess from the second recess; and
   an opening in the tray in the second recess, a material surrounding the opening being made of a material capable of elastic deformation and sized substantially equivalent to the width of the drug cartridge such that said material surrounding the opening reversibly deforms to permit insertion of the drug cartridge therethrough but would not permit removal of the cartridge by human hands without irreversibly deforming the sheet of sealable material or the opening or the tray, thereby creating a tamper-resistant drug delivery kit.

2. The improved drug delivery kit of claim 1 wherein the tray has top, bottom and side surfaces, the top and bottom surfaces being parallel to one another and the side surface being relatively perpendicular to the top and bottom surfaces, and the first and second recesses are accessible from the top surface and the opening in the second recess is located on the side surface.

3. The drug delivery kit of claim 1 wherein the opening comprises a series of intersecting slits.

* * * * *